US009820893B2

(12) United States Patent
Marquette

(10) Patent No.: US 9,820,893 B2
(45) Date of Patent: Nov. 21, 2017

(54) SANITARY PAD WITH INCREASED ABSORBABILITY

(71) Applicant: Candise K. Marquette, Sunrise, FL (US)

(72) Inventor: Candise K. Marquette, Sunrise, FL (US)

( * ) Notice: Subject to any disclaimer, the term of this patent is extended or adjusted under 35 U.S.C. 154(b) by 780 days.

(21) Appl. No.: 14/077,929

(22) Filed: Nov. 12, 2013

(65) Prior Publication Data

US 2014/0058347 A1 Feb. 27, 2014

Related U.S. Application Data

(62) Division of application No. 13/029,681, filed on Feb. 17, 2011, now abandoned.

(51) Int. Cl.

| A61F 13/15 | (2006.01) |
|---|---|
| A61F 13/20 | (2006.01) |
| A61F 13/472 | (2006.01) |
| A61L 15/28 | (2006.01) |
| A61L 15/60 | (2006.01) |
| A61F 13/45 | (2006.01) |
| A61F 13/536 | (2006.01) |

(52) U.S. Cl.
CPC ........ *A61F 13/47227* (2013.01); *A61F 13/45* (2013.01); *A61F 13/536* (2013.01); *A61L 15/28* (2013.01); *A61L 15/60* (2013.01)

(58) Field of Classification Search
CPC .......... A61F 13/47218; A61F 13/47272; A61F 2013/530437; A61F 13/47236; A61F 13/45; A61F 13/47227; A61F 13/536

USPC .................... 604/358, 385.01, 367
See application file for complete search history.

(56) References Cited

U.S. PATENT DOCUMENTS

| 2,787,271 A | 4/1957 | Clark |
|---|---|---|
| 3,600,259 A * | 8/1971 | Smith .................. A41D 31/02 |
| | | 428/103 |
| 4,285,343 A | 8/1981 | McNair |
| 4,673,403 A | 6/1987 | Lassen et al. |
| 5,211,641 A | 5/1993 | Roos et al. |
| H001585 H | 8/1996 | Ahr |
| 5,599,337 A | 2/1997 | McCoy |
| 5,675,079 A | 10/1997 | Gilman et al. |

(Continued)

FOREIGN PATENT DOCUMENTS

WO   2007/123569   * 11/2007   ............. A61F 13/15

*Primary Examiner* — Michele M Kidwell
(74) *Attorney, Agent, or Firm* — Jacqueline Tadros; Jacqueline Tadros, P.A.

(57) ABSTRACT

A multi layered sanitary pad having a unique shape and design for snug fit, increased absorption, comfort, obscurity and enhanced leak prevention that includes a body made up of embossed fleece layers. The upper surface of the sanitary pad includes a central protrusion extending longitudinally and laterally from end to end and side to side, the cross-shaped protrusion including additional cotton wadding, for increased absorption and leak prevention for extended wear. The top surface protrusion is shaped and sized to slightly penetrate the vaginal opening to ensure a snug comfortable fit to increase absorption and enhance leakage prevention along with extended wear. The top surface includes (4) recessed portions surrounding the central protrusion area, for a snug fit, additional absorption, leakage prevention and comfort.

10 Claims, 3 Drawing Sheets

(56) References Cited

U.S. PATENT DOCUMENTS

| | | | |
|---|---|---|---|
| 5,688,259 A | 11/1997 | Osborn, III et al. | |
| 5,916,205 A | 6/1999 | Olson et al. | |
| 6,114,597 A | 9/2000 | Romare | |
| 6,270,486 B1 | 8/2001 | Brown et al. | |
| 6,316,688 B1 * | 11/2001 | Hammons | A61F 13/47227 604/378 |
| 6,890,326 B2 | 5/2005 | White | |
| 7,754,940 B2 * | 7/2010 | Brisebois | A61F 13/47 604/378 |
| 7,942,858 B2 * | 5/2011 | Francoeur | A61F 13/533 604/385.101 |
| 8,728,050 B2 * | 5/2014 | Nitta | A61F 13/495 604/385.01 |
| 2003/0167044 A1 * | 9/2003 | Toyoshima | A61F 13/511 604/367 |
| 2004/0122403 A1 | 6/2004 | Mitchler et al. | |
| 2004/0167479 A1 | 8/2004 | Warren et al. | |
| 2008/0281287 A1 * | 11/2008 | Marcelo | A61F 13/4756 604/383 |
| 2011/0313385 A1 | 12/2011 | Hammons et al. | |
| 2012/0041405 A1 * | 2/2012 | Alkmin | A61F 13/15626 604/383 |
| 2012/0059344 A1 | 3/2012 | Seo | |
| 2012/0215195 A1 * | 8/2012 | Lira | A61F 13/47227 604/385.03 |
| 2012/0302984 A1 | 11/2012 | Lavash | |
| 2013/0165885 A1 | 6/2013 | Kurihara | |
| 2013/0231622 A1 | 9/2013 | Dieringer et al. | |

* cited by examiner

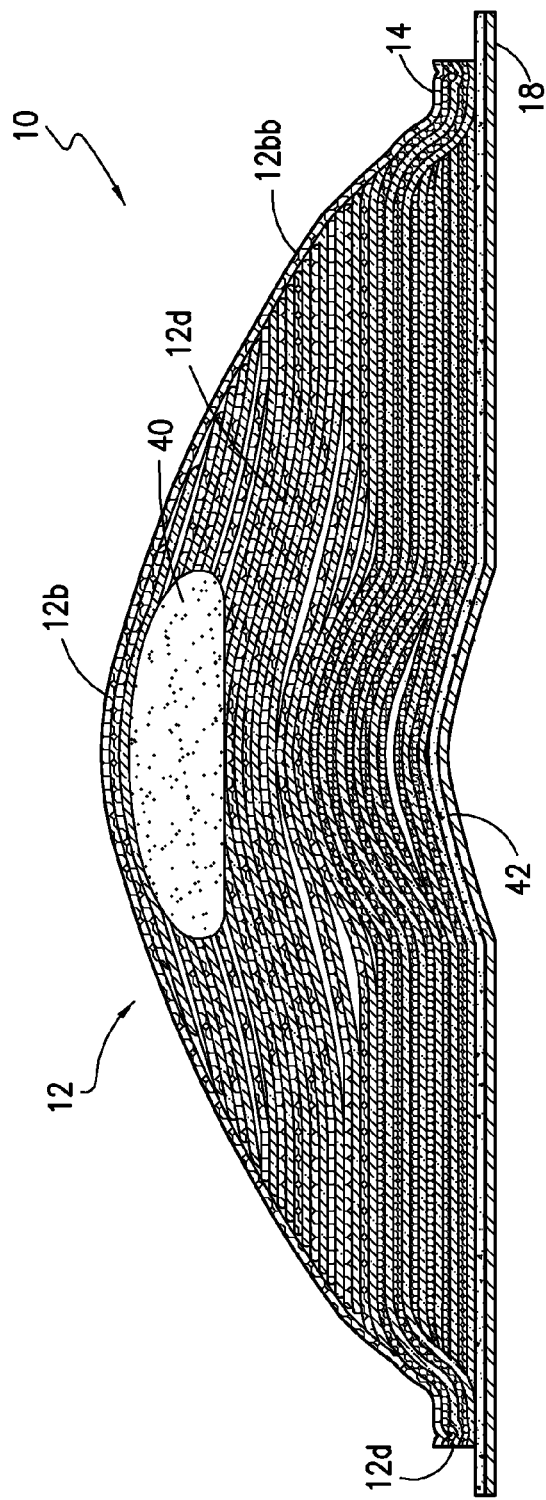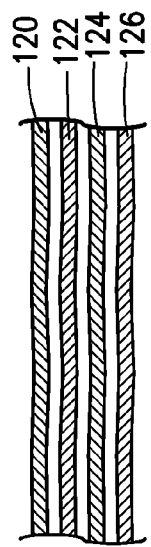

SANITARY PAD WITH INCREASED ABSORBABILITY

CROSS-REFERENCE TO RELATED APPLICATION

This is a divisional of co-pending U.S. patent application Ser. No. 13/029,681 (the '681 application), filed on Feb. 17, 2011 and entitled SANITARY PAD WITH INCREASED ABSORBABILITY. Applicant claims the benefit of the priority date of the '681 application, under Title 35, United States Code Section 120 and 37 CFR 1.78(a)(1)-(a)(3). An entire copy of the '681 application is incorporated herein by reference.

BACKGROUND OF THE INVENTION

1. Field of the Invention

This invention relates generally to a sanitary pad for absorbing feminine menstrual discharge, and specifically to a sanitary pad having a unique shape and design to ensure a snug fit, increased absorbability, reliability from leakage, and comfort and obscurity.

2. Description of Related Art

The use of sanitary pads for absorbing feminine menstrual discharge is well known in the prior art. Billions of women throughout the world experience a monthly period producing menstrual discharge. The primary goal of a sanitary pad is to absorb the menstrual discharge in a complete, discreet and comfortable manner without embarrassing leakage or unsightly bulk. Numerous different structural sanitary pads have been disclosed and used in the prior art. Vaginal devices that absorb liquids are used that are inserted into the vagina to absorb discharge. Many women do not like using the vaginal inserts because of discomfort, hygiene and religious reasons. Sanitary pads based on their current construction mounted adjacent the labia often cannot adequately snugly fit the vaginal opening so as to ensure maximum absorption and to prevent embarrassing leakage, and virtual obscurity within the vaginal and crotch area.

The sanitary pad disclosed herein based on its structure, unique design and size, has increased absorbability, leak prevention, enhanced comfort and obscurity.

SUMMARY OF THE INVENTION

A sanitary pad comprising a contoured oval shaped, elliptical body having a plurality of thin very pliant cotton layers, and said layers comprising of a cotton fleece layer, cotton wadding layer, cellulose/SAF/SAP layer, and a cotton weave layer. These layers are to be alternately thusly plied a multiplicity of times (approximately 4-5), and in varying degrees of thickness, all of which can be optionally covered with another thin cotton weave and/or gauze layer, and joined together on its outer edges. These layers shall be combined with a biodegradable cellulose/polyethylene back sheet with adhesive on its underside, and the release paper on its very bottom layer. Each pad shall have a separate pouch/wrapper for disposal.

The 4 layers comprising the upper portion, having an embossed fleece surface (top) of the sanitary pad that contacts the vaginal opening and labia has a tufted, deep dimpled surface configuration with four deep dimples forming a central convex protrusion with deep recesses on all four sides for a snug fit, comfort, and increased absorbability when the sanitary pad's top surface is in position against the vaginal opening and labia.

The shape of the contoured oval pad shall be constructed to be convex on its topside and concave on its underside for providing a unique snug and comfortable fit, and to enhance leak prevention. The contoured oval pad shall be very soft, pliant and flexible. The last bottom layer shall form a back sheet in a liquid impermeable, preferably biodegradable material, which shall be larger in size than the cotton layered portion of the pad so as to capture excess menstrual fluid, and thus enhance leak prevention.

The bottom pad cotton weave surface shall be attached to the liquid barrier sheet. This sheet shall have an adhesive underside covered by a removable release sheet that protects the adhesive until the time of use that once removed will allow the pad to be adhesively attached to the panties of the wearer.

Each sanitary pad can have a minimum of (4-5) thin layers, each layer being plied one on top of the other in a particular fashion so as make up (1) one contoured oval pad to be secured around its edge by adhesive, crimping, needle punched, or sewn. The very (top) cotton wadding layer shall be layered much thicker than the fleece and weave layers to provide a quilting or tufting of the deeply dimpled surface configuration on the top surface of the oval pad.

The sanitary pad can be constructed in different contoured oval or elliptical sizes but a standard size may be approximately 5 inches long (127 millmeters) and a small size no smaller than 3½ inches long (88.89 millimeters) can be adequately used by women and girls respectively, of different body types.

The sanitary pad is used with a pair of panties in normal use or a modest bathing suit bottom by applying of the pad in the crotch. The upper contoured oval shape of the sanitary pad fits snugly against the labia and covers the vaginal opening from the pubic mound to the anus while protruding into the vagina to ensure leakage prevention, but still maintain maximum comfort and remain obscure.

The sanitary pad's upper top surface protrusion formed by four deeply dimpled needle punched/stamped recesses is approximately ¾ to 1" inch in height. The height can vary depending on the size of the pad and the degree of absorption desired. The pocket recesses surrounding the top central protrusion, aids in the absorption of menstrual discharge, which is further enhanced by the cellulose/SAF/SAP located directly underneath the cotton wadding layer, to provide a wicking effect and further prevent exterior leakage in conjunction with the biodegradable polyethylene liquid barrier forming the very bottom layer of the sanitary pad. The top central protruding area of the sanitary pad has a nipple-shaped center with edges that fan out to make the appearance of a cross. SAF refers to super absorbent fluff which may include a drying agent, such as cellulose or an SAP.

Each sanitary pad may be constructed using individual thin layers of cotton. An example of suitable cotton layers is described in U.S. Pat. No. 7,192,630 (B2) FIGS. 1 and 2. In the present invention the shape of the pad shall be contoured oval or elliptical, comprising of all the individual layers of cotton being cut to the contoured oval design. Preferably the layering of the present invention would have a basic structure of the patent herein above-referenced.

It is an object of this invention to provide a sanitary pad using thin pliant cotton layers and a uniquely contoured oval shape for a snug and obscure fit, increased absorbability and reliable against leakage.

It is another object of this invention to provide a sanitary pad that is biodegradable and highly absorbent made of natural and/or organic cotton, comfortable and reliable against leakage.

BRIEF DESCRIPTION OF THE DRAWINGS

FIG. 3 shows a side elevational view of the invention in cross-section.
FIG. 3A shows a cutaway side elevational view of three layers of different cotton configurations and an absorption layer used in the device shown in FIG. 3.

PREFERRED EMBODIMENT OF THE INVENTION

Figure 1:
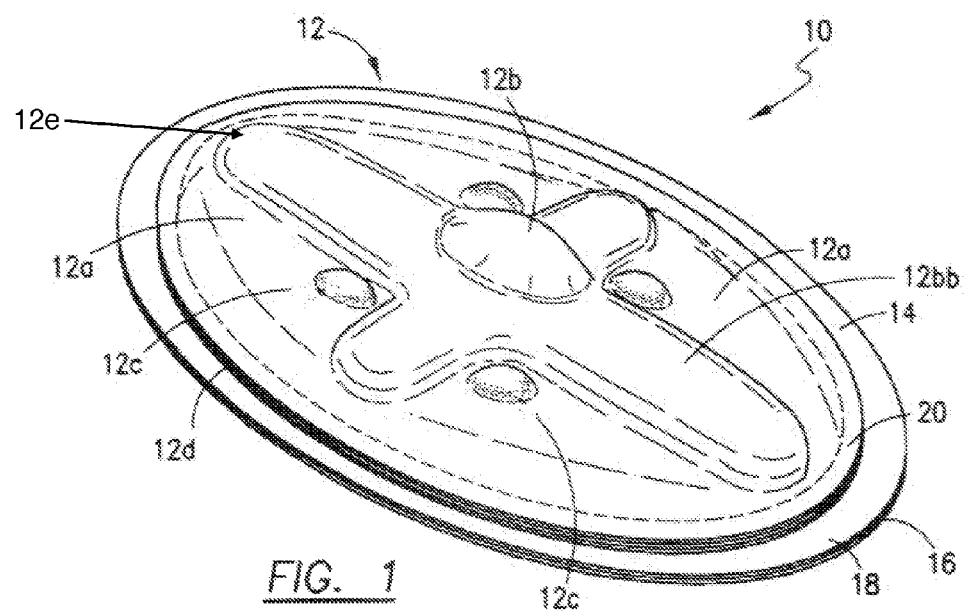
FIG. 1 shows a top perspective view of the invention.
Figure 2:
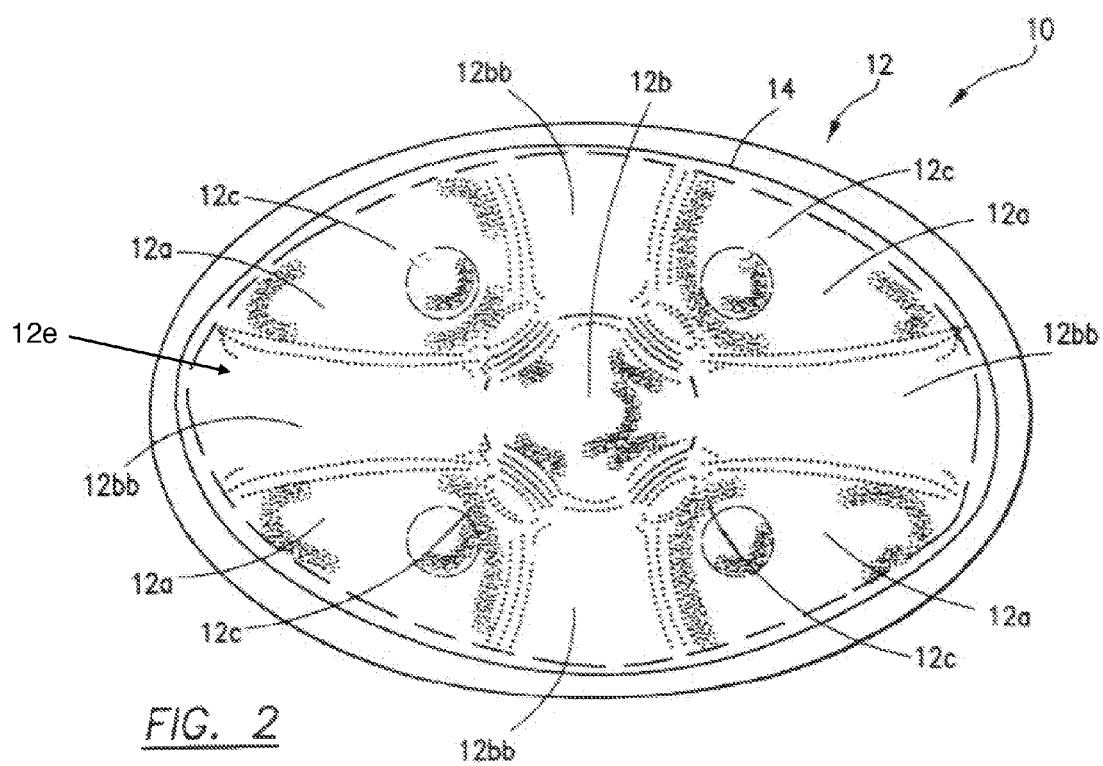
FIG. 2 shows a top plan view of the invention.

Referring now to the drawings and in particular FIGS. 1 and 2, a sanitary pad 10 is shown comprised of a contoured oval or elliptically shaped body 12 having top or upper body surface segments 12a, around the top surface of the sanitary pad, and a central raised portion that includes a liquid absorbing nipple shaped protrusion 12b with longitudinal and lateral extensions 12bb that extend end to end and side to side forming a cross shaped top protrusion. The raised areas 12bb and liquid absorbing nipple shaped protrusion 12b in a center position form a cross shaped protrusion and are surrounded by recesses 12c formed on all four sides of the liquid absorbing nipple shaped protrusion 12b. The top area of the sanitary pad is made of a thin cotton contoured oval layer 12a.

The top or upper body surface segments 12a and liquid absorbing nipple shaped protrusion 12b and longitudinal and lateral extensions 12bb of the sanitary pad 10 in use engage the vaginal opening and labia.

The bottom of the sanitary pad 10 includes a liquid barrier 14 that extends outwardly around the periphery of the body 12 as a peripheral extension that overlaps the bottom edge of the body 12. The liquid barrier 14 is a thin sheet of liquid impervious material such as biodegradable cellulose/polyethylene to prevent leakage.

The underside bottom surface of the liquid barrier 14 has adhesive 16 deposited thereon used to attach the entire body 12 to the crotch of the user's underwear. A cover 18 that acts as a layer of protective material, such as a release paper that can be removed from the adhesive 16 at the time of use protects the adhesive until time of use.

A plurality of thin cotton contoured oval layers 12d form the body 12 of the sanitary pad 10. Each of the thin cotton contoured oval layers 12d is elliptical in shape. The top of the body 12 has the liquid absorbing nipple shaped protrusion 12b and the longitudinal and lateral extensions 12bb. The longitudinal and lateral extensions 12bb form the cross shaped protrusion 12e which is accentuated by four recesses 12c which also collect fluids and liquid, increasing absorption and comfort. The top surface recesses 12c are formed by needle punch, stamping, or crimping. The multi layers of the thin cotton contoured oval pads such as layer 12d are joined together in a laminate also by crimping/adhesive/needle punch and are explained in detail below. The crimping/adhesive/needle punches 20 are shown by dashed lines surrounding the periphery of the sanitary pad made of the thin layers of cotton contoured oval layers joined around their peripheries by crimping/adhesive/needle punch. The thin layers can be glued or bonded together by crimping/adhesive/needle punch.

The very bottom layer of the sanitary pad 10 includes an enlarged contoured oval that has a liquid barrier 14 attached to the bottom of the body 12. The oval liquid barrier 14 extends well beyond the edge of the periphery of the contoured body 12 area of the sanitary pad 10. This is to provide overlap to prevent leakage. Attached to one side of the liquid barrier 14 is an adhesive 16 protected by the cover 18 that is removed at time of use so that the adhesive 16 can be used to attach the entire sanitary pad 10 into the crotch of a pair of panties to prevent shifting or movement.

The overall construction of the sanitary pad 10 includes the area of the liquid absorbing nipple shaped protrusion 12b formed by the body 12 which is formed from one or more cotton layers. Note that the interior of the liquid absorbing nipple shaped protrusion 12b and longitudinal and lateral extensions 12bb may be made of cotton wadding 40 that is stuffed in between a top thin cotton contoured oval embossed and weave layers.

Referring now to FIG. 3, the overall construction of the sanitary pad can be viewed in cross-section. The area of the liquid absorbing nipple shaped protrusion 12b central circular nipple shape is formed by semi-spherical shaped volume stuffed with cotton wadding 40 which may include one or more cotton layers like that of a very thick cotton ball, which is then needle punched/stamped in the four (4) center areas, forming a box, that is pushed down into the attached oval cotton pad forming the liquid absorbing nipple shaped protrusion 12b.

As shown in FIG. 3, sanitary pad 10 includes body 12 which includes a central layer of cotton wadding 40 shown at a central point of the sanitary pad 10 at the liquid absorbing nipple shaped protrusion 12b whereby the cotton wadding 40 would taper and extend from one end to the other longitudinally and laterally. The cotton wadding 40 is thickest in the middle. The central cotton wadding 40 is surrounded by multiple layers of thin contoured oval layers 12d.

The very bottom of the body 12 of the sanitary pad 10 includes a liquid barrier 14 having a liquid impervious layer of biodegradable cellulose/polyethylene, which acts and is in essence a panty-liner preventing the liquid absorbed into the sanitary pad 10 from leaking out the bottom and periphery of the sanitary pad 10. The various layers of thin cotton contoured oval pads 12d are connected around the pad periphery by adhesive/crimping/needle punch 20 as shown in FIG. 1. In an alternate embodiment, the layers could also be attached by an adhesive and heat sealed around the periphery of the body 12 of the sanitary pad 10.

With the structure shown in FIG. 3, the amount of absorbency of each sanitary pad 10 is greatly increased by having separate large internal areas with cotton wadding 40 located along the top underneath liquid absorbing nipple shaped protrusion 12b. In addition, each of the cotton pad layers which are thin contoured oval layers is made out of cotton, which can be textured to give strength, durability, and also absorb body fluid.

FIG. 3 shows the layered use of different cotton contoured oval shaped layers using the four different layers shown in FIG. 3A repetitively from bottom to top of the pad in a single pad. Also shown is a central layer of cotton wadding 40 to make the liquid absorbing nipple shaped protrusion 12b a raised cross shape on the top surface of the sanitary pad 10.

In FIG. 3A, typically the layers include an embossed cotton contoured oval layer 120, a thin cotton wadding contoured oval layer 122, a cellulose/SAF/SAP powder thin absorption layer 124, and a weave cotton contoured oval layer 126. This core layered pattern is repeated several times in the construction of the sanitary pad 10 comprising of a minimum total of 16 individual layers to 24 or more individual layers. FIG. 3 is a schematic drawing not necessarily to scale to show the basic contoured oval construction of a sanitary pad 10 that includes representations of the individual layers described above, the liquid absorbing nipple shaped protrusion 12b, the longitudinal and lateral extensions 12bb, a central layer of cotton wadding 40, all having a concave base or bottom area 42 that gives the sanitary pad 10 increased structural shape. The cotton contoured oval layers that make up the core of the sanitary pad 10 as shown in FIG. 3 and FIG. 3A include an embossed cotton contoured oval thin layer 120, the thin contoured oval cotton wadding layer 122, a layer of cellulose/SAF/SAP 124 for absorption, and a thin cotton contoured oval weave layer 126. By using a core of thin cotton absorbent layers that is repeated again and again in the construction of the sanitary pad 10, the sanitary pad 10 is highly absorbent, directing the flow downwardly towards the impervious liquid barrier 14 to greatly increase the amount of liquid that the sanitary pad 10 can absorb. This four layer core pattern shown in FIG. 3A is repeated from the top of the sanitary pad 10 to the bottom of the sanitary pad 10. All of the cotton contoured oval layers of the sanitary pad 10 are connected together along the periphery or outside edge of the sanitary pad 10 preferably by adhesive/crimping/needle punch. However, all of the layers of the sanitary pad 10 can be individually layered and then glued/crimped/needle punched together all the way around the periphery of the sanitary pad 10 and compressed/crimped/stamped slightly to join the thin layers together.

The entire body 12 of the sanitary pad 10 can include an outer cotton contoured oval weave top sheet as a covering for holding the body 12 together as a unit in conjunction with the bottom surface which is a biodegradable polyethylene liquid barrier 14 pantiliner back sheet that is joined to the outer cotton contoured oval weave to form a single integral unit. The outer cotton weave is a cotton contoured oval top sheet that itself would be comfortable when in contact with the vaginal opening and the labia, being soft and resilient and pliable.

The very bottom liquid barrier 14 prevents leakage. The liquid barrier 14 can be contoured and oval shaped and larger in circumference with an overlapping area than the layers of cotton contoured sanitary pad 10 so that the liquid barrier 14 overlaps the outer periphery of the body 12, again to prevent leakage.

Figure 4:
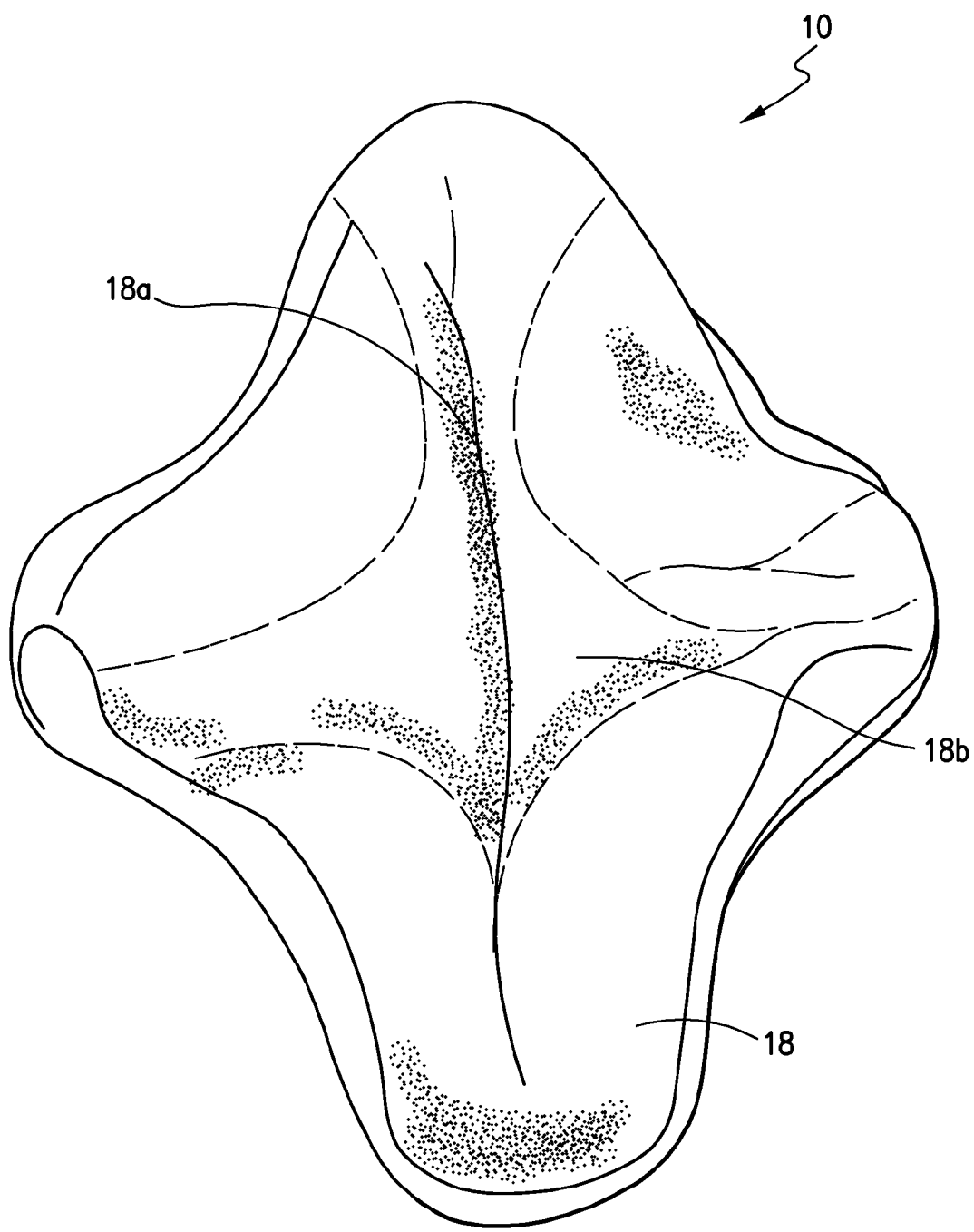
FIG. 4 is a bottom plan view of the invention.

FIG. 4 shows the bottom concave side of the sanitary pad 10 which includes the barrier 14. Initially the sanitary pad 10 bottom is covered with protective release paper or the cover 18 which may be biodegradable cellulose/polyethylene that hides adhesive 16 disposed on the outside surface of the liquid barrier 14. At the time of use, the cover 18 is removed, exposing the liquid barrier 14 and adhesive 16 which is used to attach the body 12 to the crotch of the user's underpants. Note areas 18a and 18b. The bottom side of the sanitary pad 10 has concave channels 18a longitudinally and laterally 18b to give the sanitary pad 10 some structural form. The concavity is not extremely pronounced but could be three fourths of an inch to a 1 inch deep in the middle area of the bottom of the sanitary pad 10. The liquid barrier 14 has adhesive 16 attached to the cover 18 which may be a removable protective release sheet that is removed at the time of use so the sanitary pad 10 can be attached to the crotch of the user's panties.

FIG. 1 can also be used to describe an alternative embodiment of the invention used as a panty liner 50. The device includes a liquid barrier 14 layer made of cellulose/polyethylene having a protective bottom paper cover 18 to protect an adhesive 16 layer on the liquid barrier 14 layer. The panty liner may be constructed of only four layers. Typically the layers include an embossed cotton contoured oval layer 120, a thin cotton wadding contoured oval layer 122, a cellulose/SAF/SAP powder thin layer 124, and a weave cotton contoured oval layer 126 as shown in FIG. 3A. With the panty liner, the four layers of FIG. 3A make up the panty liner plus the liquid barrier as shown in FIG. 1.

Referring back to FIG. 1, the front to back and side to side longitudinal and lateral extensions 12bb in conjunction with the liquid absorbing nipple shaped protrusion 12b are sized to slightly penetrate the vaginal opening for maximum absorption, snug fit, and increased comfort.

The instant invention has been shown and described herein in what is considered to be the most practical and preferred embodiment. It is recognized, however, that departures may be made there from within the scope of the invention and that obvious modifications will occur to a person skilled in the art.

What is claimed is:

1. A multi layered sanitary pad comprising: a body including a cross-shaped protrusion, wherein the cross-shaped protrusion is in a central position of the sanitary pad, for penetrating a vaginal opening, thereby ensuring a snug, comfortable fit for increased absorption, enhanced leakage prevention and extended wear, wherein the cross-shaped protrusion includes longitudinal extensions and lateral extensions, wherein the longitudinal extensions extend longitudinally from a first end of the body to a second end of the body, and wherein the lateral extensions extend laterally across the entire body from a first side of the body to a second side of the body, the cross-shaped protrusion thereby segmenting the body into four quadrants.

2. The sanitary pad of claim 1, wherein the body includes cotton embossed fleece layers, wadding layers, cellulose/SAF/SAP layers and weave layers.

3. The sanitary pad of claim 1, wherein the plurality of recesses are formed by needle punch stamping.

4. The sanitary pad of claim 1, wherein a plurality of recesses are positioned around the cross-shaped protrusion.

5. The sanitary pad of claim 1, wherein the cross shaped protrusion includes a nipple center.

6. The sanitary pad of claim 1, wherein the cross shaped protrusion in a central position of the sanitary pad engages the vaginal opening and labia when the sanitary pad is in use.

7. The sanitary pad of claim 5, wherein the nipple center is formed by a semi-spherical shaped volume filled with cotton wadding, including one or more cotton layers, wherein the one or more cotton layers are needle stamped in each of the four quadrants.

8. The sanitary pad of claim 1, wherein a bottom layer of the sanitary pad further includes concave channels relative to a bottom side of the sanitary pad, and wherein the concave channels project longitudinally and laterally.

9. The sanitary pad of claim 4, wherein four recesses are positioned around the cross-shaped protrusion, with one recess located in each of the four quadrants.

10. A sanitary pad comprising:
a liquid pervious side;
a liquid impervious side opposite the liquid pervious side, wherein the liquid pervious side and the liquid impervious side are arranged to form a unitary structure; and
a cross-shaped absorbent protrusion, wherein the cross-shaped protrusion is in a central position of the sanitary pad, whereby the cross-shaped protrusion includes longitudinal extensions that extend longitudinally from a first end of the body to a second end of the body and lateral extensions that extend laterally across the entire body from a first side of the body to a second side of the body in a transverse direction relative to the longitudinal extensions.

\* \* \* \* \*